United States Patent
Palushi et al.

(10) Patent No.: US 11,944,769 B2
(45) Date of Patent: Apr. 2, 2024

(54) STEERABLE GUIDE WITH PARTIAL SLEEVE

(71) Applicant: Acclarent, Inc., Irvine, CA (US)

(72) Inventors: Jetmir Palushi, Irvine, CA (US); Fatemeh Akbarian, Rancho Palos Verdes, CA (US); Behnam Amin, Mission Viejo, CA (US); George L. Matlock, Laguna Hills, CA (US)

(73) Assignee: Acclarent, Inc., Irvine, CA (US)

(*) Notice: Subject to any disclaimer, the term of this patent is extended or adjusted under 35 U.S.C. 154(b) by 583 days.

(21) Appl. No.: 17/067,872

(22) Filed: Oct. 12, 2020

(65) Prior Publication Data

US 2021/0138212 A1    May 13, 2021

Related U.S. Application Data

(60) Provisional application No. 62/934,005, filed on Nov. 12, 2019.

(51) Int. Cl.
*A61M 29/02* (2006.01)
*A61B 17/24* (2006.01)
(Continued)

(52) U.S. Cl.
CPC ............. *A61M 29/02* (2013.01); *A61B 17/24* (2013.01); *A61M 25/10* (2013.01);
(Continued)

(58) Field of Classification Search
CPC .................. A61M 29/02; A61M 25/10; A61M 2029/025; A61B 2017/00314;
(Continued)

(56) References Cited

U.S. PATENT DOCUMENTS

| | | | | |
|---|---|---|---|---|
| 4,711,406 A | * | 12/1987 | Barstow | B65H 75/246 403/279 |
| 5,381,782 A | * | 1/1995 | DeLaRama | A61B 1/0056 604/95.01 |
| 7,381,198 B2 | | 6/2008 | Noriega et al. | |
| 7,840,261 B2 | | 11/2010 | Rosenman et al. | |
| 9,155,492 B2 | | 10/2015 | Jenkins et al. | |
| 9,757,018 B2 | | 9/2017 | Kesten et al. | |
| 10,610,308 B2 | | 4/2020 | Sema et al. | |

(Continued)

FOREIGN PATENT DOCUMENTS

WO   WO 1999/011313 A1   3/1999

OTHER PUBLICATIONS

International Search Report and Written Opinion dated Feb. 3, 2021, for International Application No. PCT/IB2020/060618, 14 pages.

*Primary Examiner* — Anh T Dang
(74) *Attorney, Agent, or Firm* — Frost Brown Todd LLP

(57) ABSTRACT

A catheter system includes a body, a guide member assembly, an articulation assembly, and a partial sleeve. The guide member assembly extends distally from the body and includes a proximal rigid portion defining a longitudinal axis, a distal flexible portion, and an open distal end. The guide member assembly defines a lumen in communication with the body and the open distal end. The articulation section can flex the distal flexible portion and the open distal end relative to the longitudinal axis between a straight configuration and an articulated configuration. The partial sleeve is disposed within a portion of the lumen defined by the distal flexible portion. The partial sleeve also defines a longitudinally extending gap.

16 Claims, 13 Drawing Sheets

(51) Int. Cl.
  *A61M 25/10*  (2013.01)
  *A61B 17/00*  (2006.01)
  *A61M 25/01*  (2006.01)

(52) U.S. Cl.
  CPC .............. *A61B 2017/00314* (2013.01); *A61B 2017/00323* (2013.01); *A61B 2017/00336* (2013.01); *A61B 2017/00862* (2013.01); *A61B 2217/005* (2013.01); *A61B 2217/007* (2013.01); *A61M 2025/015* (2013.01); *A61M 2029/025* (2013.01)

(58) Field of Classification Search
  CPC ........... A61B 2017/00323; A61B 2017/00336; A61B 2017/00862
  See application file for complete search history.

(56) References Cited

U.S. PATENT DOCUMENTS

| | | | |
|---|---|---|---|
| 2007/0225750 A1* | 9/2007 | Ren | A61F 2/013 606/200 |
| 2008/0300462 A1 | 12/2008 | Intoccia et al. | |
| 2010/0217261 A1* | 8/2010 | Watson | A61M 25/0147 604/95.04 |
| 2017/0258618 A1 | 9/2017 | Dann et al. | |
| 2018/0001058 A1* | 1/2018 | Schlesinger | A61B 34/74 |
| 2018/0214082 A1 | 8/2018 | Burkett et al. | |
| 2018/0311472 A1 | 11/2018 | Matlock et al. | |
| 2019/0015645 A1 | 1/2019 | Matlock et al. | |
| 2019/0091438 A1 | 3/2019 | Higgins et al. | |

* cited by examiner

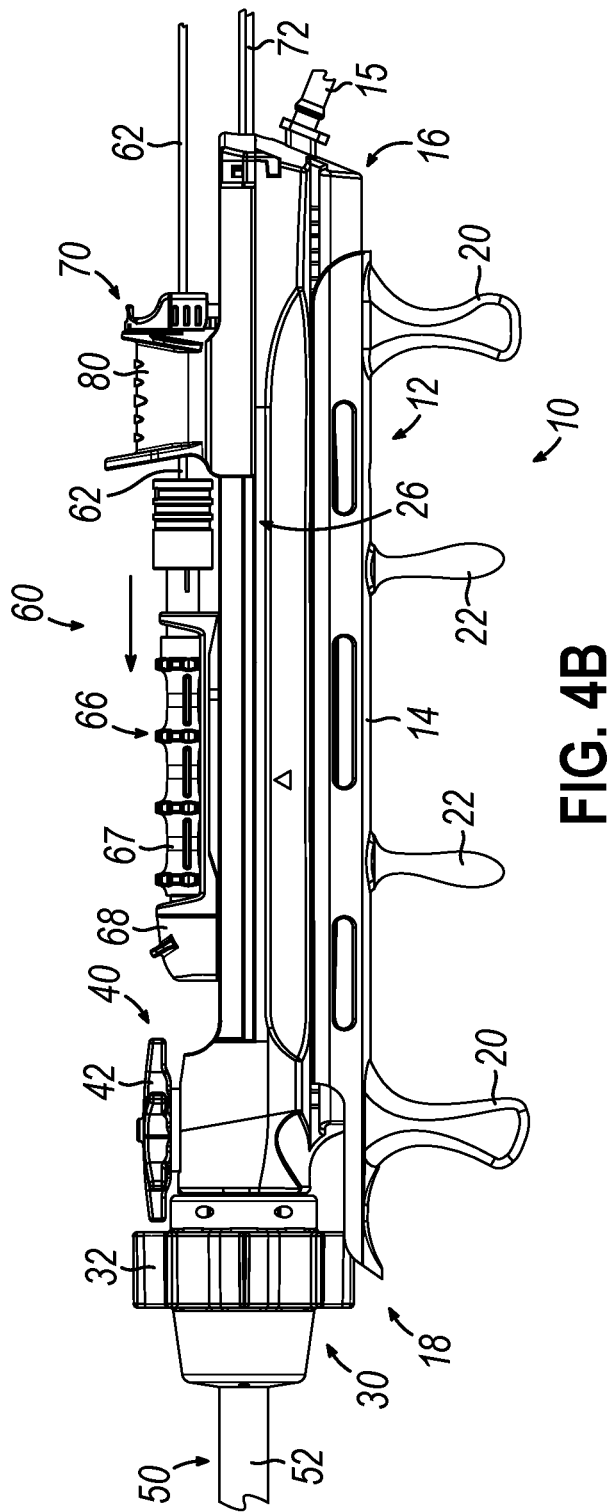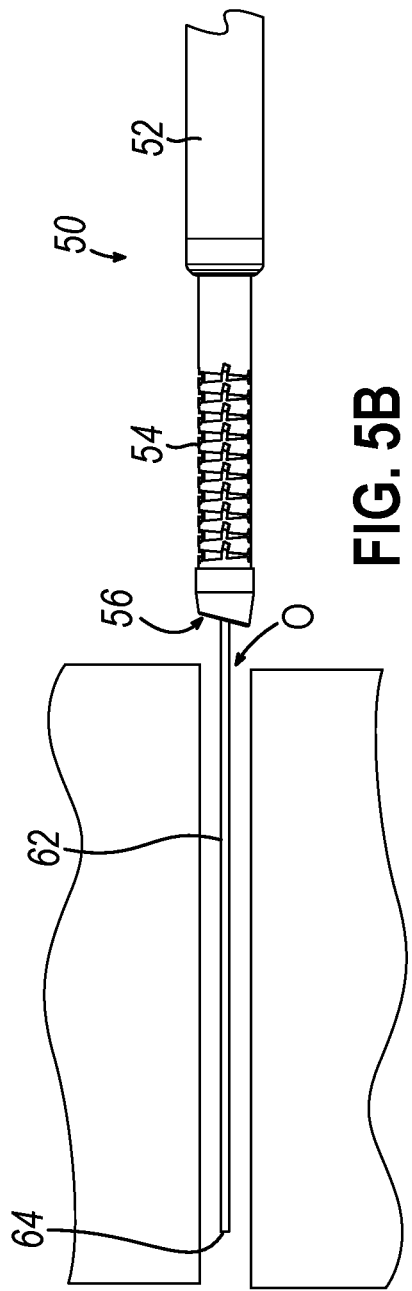

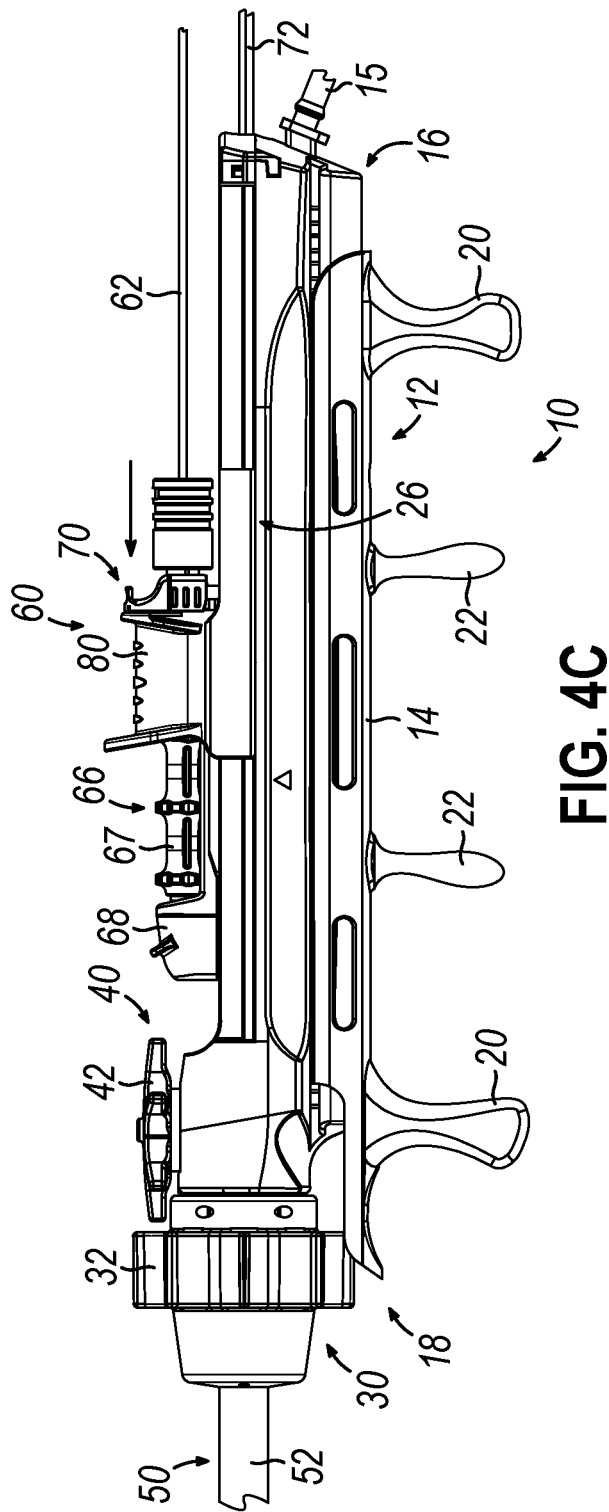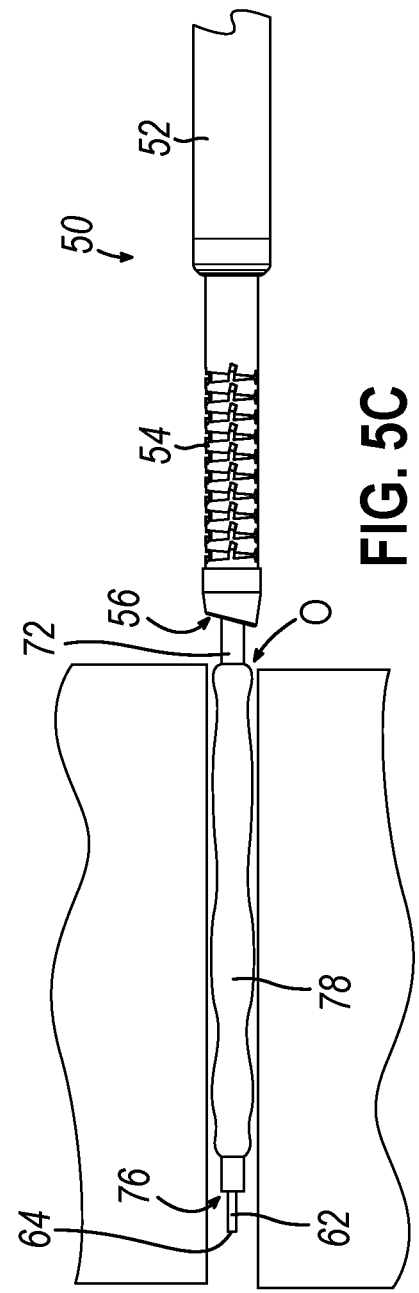
FIG. 4C
FIG. 5C

STEERABLE GUIDE WITH PARTIAL SLEEVE

PRIORITY

This application claims priority to U.S. Provisional Pat. App. No. 62/934,005, entitled "Steerable Guide With Partial Sleeve," filed on Nov. 12, 2019, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site.

While several systems and methods have been made and used to access and dilate anatomical passageways, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 4B depicts an elevational side view of the handle assembly of FIG. 1, where the guidewire movement mechanism of FIG. 4A is in a distal position, and where the dilation catheter movement mechanism of FIG. 4A is in the proximal position;

FIG. 4C depicts an elevational side view of the handle assembly of FIG. 1, where the guidewire movement mechanism of FIG. 4A is in the distal position, and where the dilation catheter movement mechanism of FIG. 4A is in a distal position;

FIG. 5B depicts an elevational side view of the open distal tip of the guide catheter assembly of FIG. 1 placed adjacent to the sinus ostium of the patient, where a distal tip of the guidewire of FIG. 5A extends distally past the open distal tip of the guide catheter assembly, and where the inflatable balloon of the dilation catheter assembly of FIG. 1 is housed within the guide catheter assembly in a deflated state;

FIG. 5C depicts an elevational side view of the open distal tip of the guide catheter assembly of FIG. 1 placed adjacent to the sinus ostium of the patient, where a distal tip of the guidewire of FIG. 5A extends distally past the open distal tip of the guide catheter assembly, and where the inflatable balloon of the dilation catheter assembly of FIG. 1 extends distally past the open distal tip of the guide catheter assembly in a deflated state;

Figure 1:
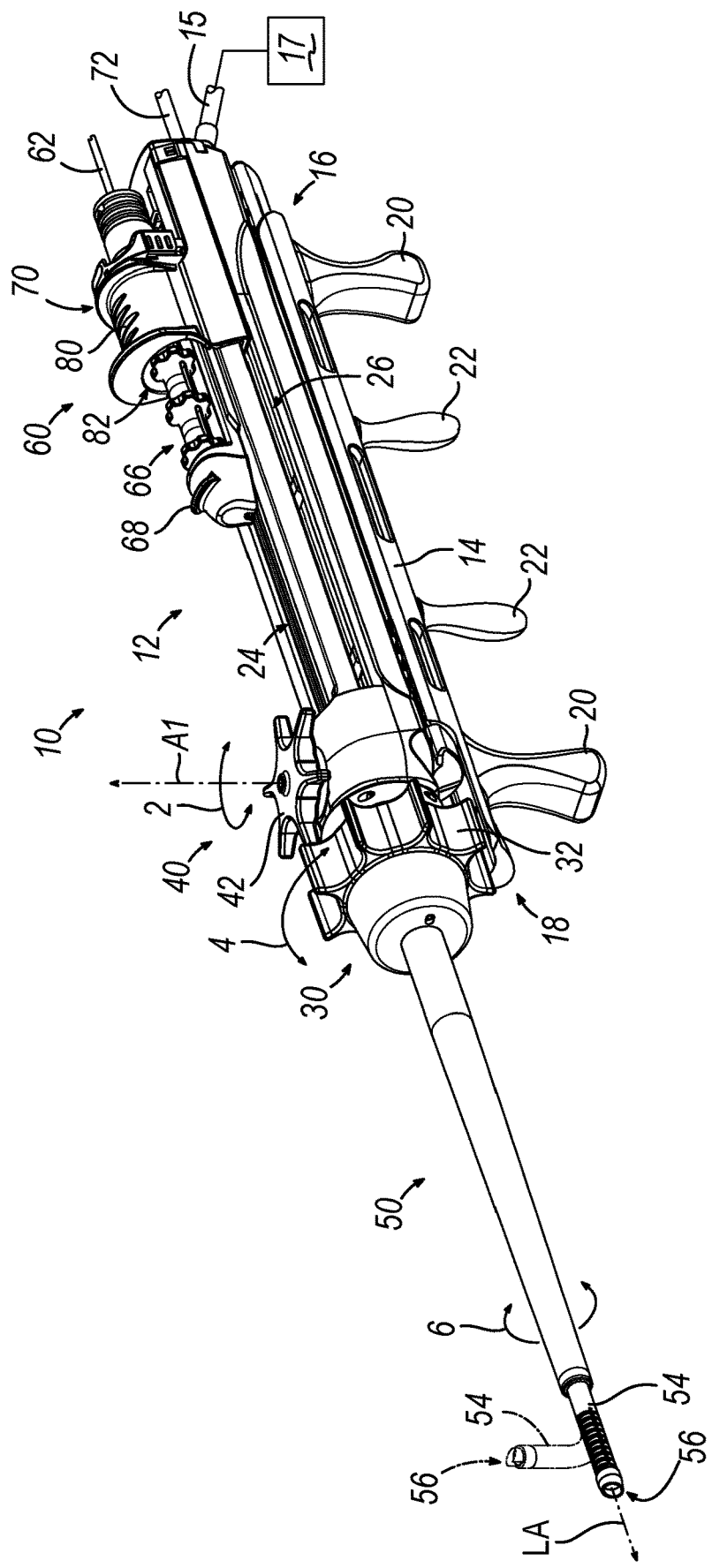
FIG. 1 depicts a perspective view of an exemplary instrument having a handle assembly, a guide catheter assembly, a guidewire assembly, and a dilation catheter assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Instrument

Figure 2:
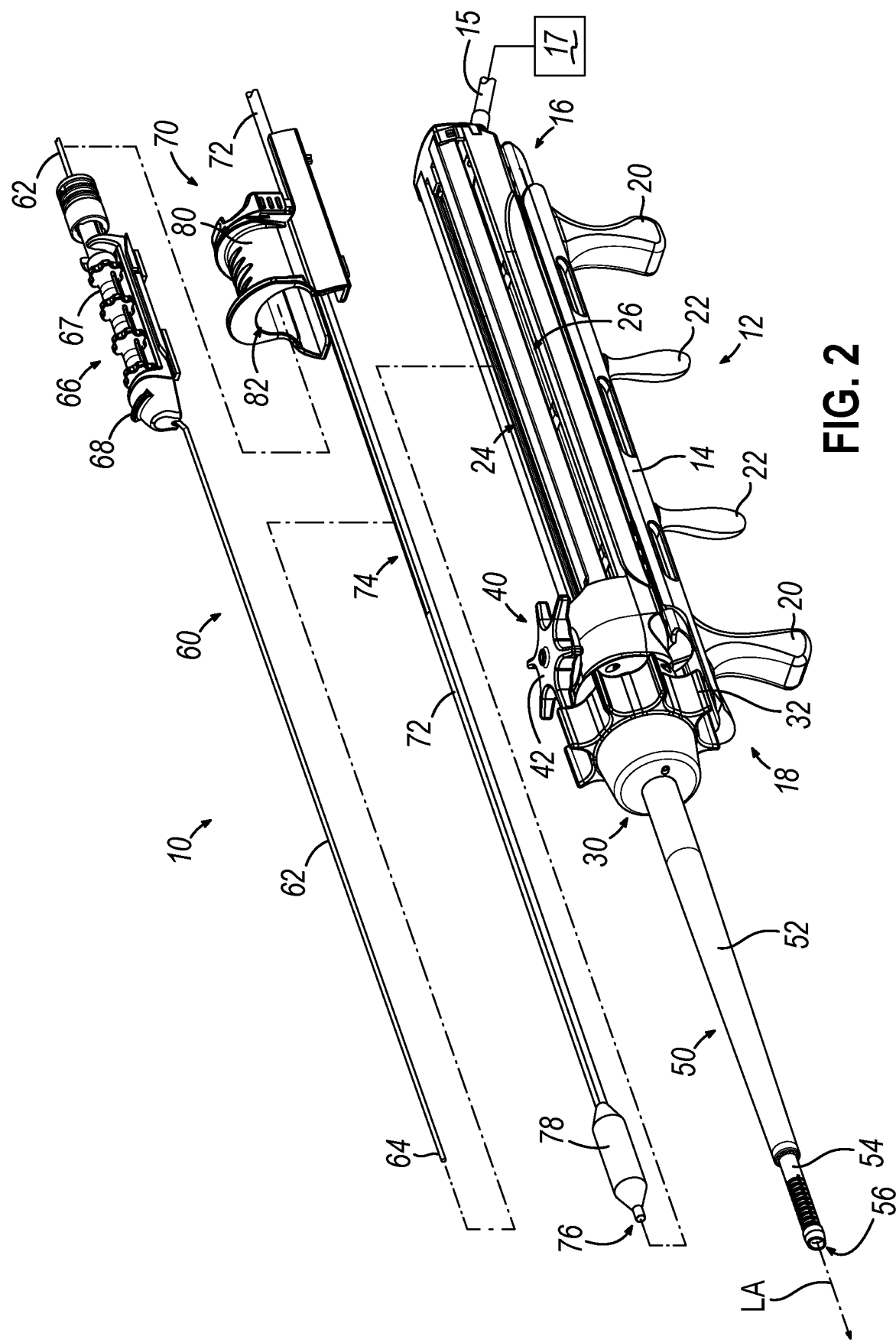
FIG. 2 depicts an exploded perspective view of the instrument of FIG. 1.

FIGS. 1-2 show an exemplary instrument (10) that may be used to provide access within or adjacent to various different anatomical passageways (e.g., frontal sinus ostium, frontal recess, maxillary sinus ostium, sphenoid sinus ostium, ethmoid sinus ostium, Eustachian tube, etc.). Instrument (10) includes a handle assembly (12), a guide catheter assembly (50), a guidewire assembly (60), and a dilation catheter assembly (70). Handle assembly (12) further includes an articulation drive assembly (30) and a rotation drive assembly (40).

As will be described in greater detail below, rotation drive assembly (40) and articulation drive assembly (30) may be used to provide access to various different anatomical passageway with the same guide catheter assembly (50) by making simple adjustments to structural features of instrument (10). As will also be described in greater detail below, handle assembly (12) may be configured to allow an operator to control the placement of guide catheter assembly (50), guidewire assembly (60), and dilation catheter assembly (70) with a single hand in order access and dilate a desired anatomical passageway.

A. Exemplary Handle Assembly and Guide Catheter Assembly

As best seen in FIGS. 1-2, handle assembly (12) includes a body portion (14) and finger pegs (20, 22) extending from body portion (14). Handle assembly (12) extends longitudinally from a proximal portion (16) to a distal portion (18). A fluid lumen (15) extends proximally from proximal portion (16) of handle assembly (12). Fluid lumen (15) is in fluid communication with an internal lumen of guide catheter assembly (50) via an internal passageway (not shown) defined by body portion (14), which is in fluid communication with guide catheter assembly (50). Fluid lumen (15) may be configured to couple with suction/irrigation source (17) such that suction/irrigation source (17) may provide suction/irrigation at open distal tip (56) of guide catheter assembly (50) during exemplary use. Other suitable ways in which fluid lumen (15) and the internal passageway of body portion (14) may be made and used will be apparent to those skilled in the art in view of the teachings herein. Finger pegs (20, 22) are configured to promote gripping of handle assembly (12) such that the operator may grasp handle assembly (12) while simultaneously controlling selected portions of guidewire assembly (60) and dilation catheter assembly (70) in accordance with the description herein.

Body portion (14) defines a first longitudinally extending track (24) and a second longitudinally extending track (26). First and second tracks (24, 26) are configured to couple with a guidewire movement mechanism (66) of guidewire assembly (60) and a dilation catheter movement mechanism (80) of dilation catheter assembly (70), respectively, such that guidewire assembly (60) and dilation catheter assembly (70) may translate relative to body portion (14) independently of each other. First track (24) is also dimensioned to slidably house a dilation catheter (72) of dilation catheter assembly (70). Dilation catheter movement mechanism (80) further defines a cavity (82) in order to allow guidewire movement mechanism (66) to translate proximally and distally through dilation catheter movement mechanism (80). In other words, movement mechanisms (66, 80) do not inhibit translation of each other relative to handle assembly (12).

Guide catheter assembly (50) extends distally from distal portion (18) of handle assembly (12). Guide catheter assembly (50) includes a rigid guide shaft portion (52) and a flexible guide shaft portion (54) terminating at open distal tip (56). Guide catheter assembly (50) defines an internal lumen extending from a proximal end of rigid guide shaft portion (52) all the way to open distal tip (56). The lumen defined by guide catheter assembly (50) is in communication with the distal portion of first track (24) in order to allow selected portions of guidewire assembly (60) and dilation catheter assembly (70) to slidably extend through handle assembly (12), guide catheter assembly (50), and distally through open distal tip (56). Guide catheter assembly (50) may be dimensioned to be inserted transnasally or transorally to provide access to suitable anatomical structures within a patient's head via open distal tip (56). In other exemplary uses, guide catheter assembly (50) is positioned elsewhere within a patient (e.g., somewhere other than within the patient's head). Various suitable locations and procedures in which instrument (10) may be used will be apparent to those skilled in the art in view of the teachings herein.

Figure 3A:
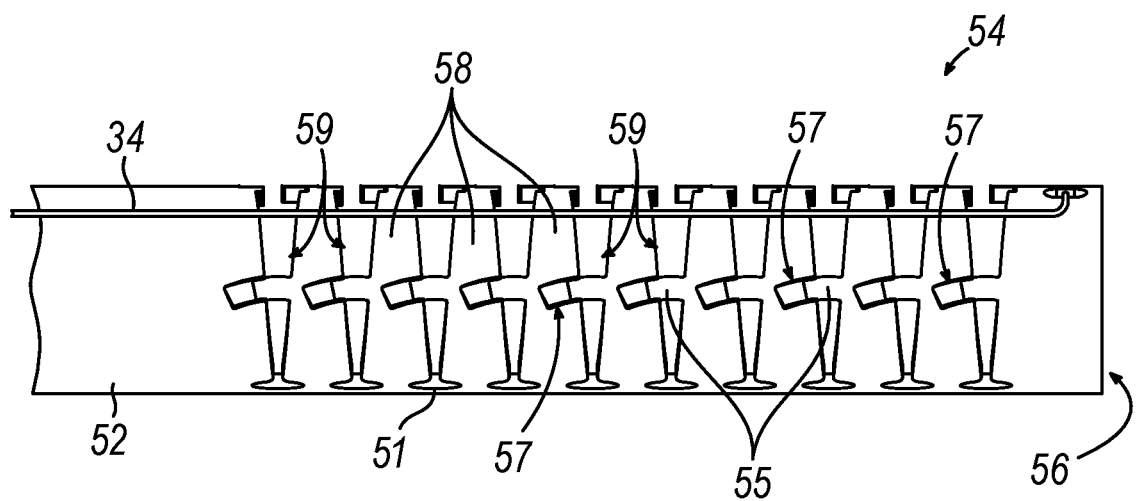
FIG. 3A depicts an elevational side view of a flexible portion of the guide catheter assembly of FIG. 1 in a straight configuration.
Figure 3B:
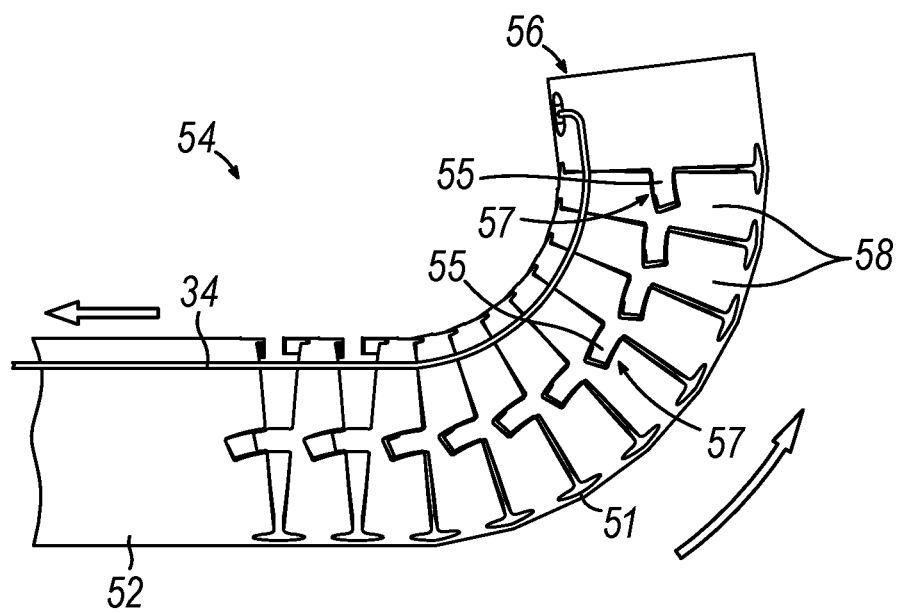
FIG. 3B depicts an elevational side view of a flexible portion of the guide catheter assembly of FIG. 1 in a bent configuration.

As best seen in FIGS. 3A-3B, flexible guide shaft portion (54) includes an array of flexing bodies (58) connected to each other via a resilient spine (51) extending between rigid guide shaft portion (52) and open distal tip (56). Resilient spine (51) is biased toward the straight, non-articulated position shown in FIG. 3A. Resilient spine (51) is sufficiently flexible to allow flexing bodies (58) to move toward and away from each other in order to deflect open distal tip (56) toward and away from longitudinal axis (LA) in accordance with the description herein. Flexing bodies (58) include complementary interlocking features (55, 57) configured to interlock with adjacent flexing bodies (58) in order to inhibit flexing bodies (58) and resilient spine (51) from bending, deflecting, flexing, etc. in any other direction besides the predetermined articulation path. In other words, complementary interlocking features (55, 57) may help promote rigidity of flexible guide shaft portion (54) while in a desired articulated position during exemplary use, while also allowing flexible guide shaft portion (54) to flex toward and away from longitudinal axis (LA) along the predefined path when the operator utilizes articulation drive assembly (30) (as exemplified between FIGS. 3A-3B).

As best seen in FIG. 3A, when flexible guide shaft portion (54) is in the non-articulated configuration (or various articulated configurations), adjacent flexing bodies (58) define respective gaps (59) in order to accommodate for further flexing of bodies (58). Gaps (59) may extend from an external portion of flexible guide shaft portion (54) into internal lumen defined by flexible guide shaft portion (54). As flexing bodies (58) move toward and away from each other in order to articulate open distal tip (56), the size of gaps (59) change. In some instances, as best shown in FIG. 3B, flexible guide shaft portion (54) may articulate open distal tip (56) to a position where gaps (59) are no longer present.

Rigid guide shaft portion (52) is coupled with a thumbwheel (42) of rotation drive assembly (40). By way of example only, rigid guide shaft portion (52) and thumbwheel (42) may be coupled together via complementary bevel gears. Such a coupling may be provided in accordance with at least some of the teachings of U.S. Pat. Pub. No. 2019/0015645, entitled "Adjustable Instrument for Dilation of Anatomical Passageway," published Jan. 17, 2019, issued as U.S. Pat. No. 10,874,839 on Jan. 29, 2020, the disclosure of which is incorporated by reference herein. Other suitable ways in which rigid guide shaft portion (52) and thumbwheel (42) may be coupled together will be apparent to those skilled in the art in view of the teachings herein.

Thumbwheel (42) of rotation drive assembly (40) is operable to rotate relative to body portion (14) about a first axis (A1), as indicated by arrow (2). Rotation of thumbwheel (42) about first axis (A1) is configured to drive rotation of guide catheter assembly (50) relative to handle assembly (12) about longitudinal axis (LA) of guide catheter assembly (50), as indicated by arrow (6). Therefore, an operator may rotate guide catheter assembly (50) about longitudinal axis (LA) in order to selectively position open distal tip (56) relative to handle assembly (12). Other suitable features that may be used to provide rotation of guide catheter assembly (50) will be apparent to those skilled in the art in view of the teachings herein. Alternatively, instrument (10) may be configured such that guide catheter assembly (50) is not rotatable relative to handle assembly (12).

As yet another merely illustrative example, instrument (10) may be configured such that knob (32) of articulation drive assembly (30) is operable to drive rotation of guide catheter assembly (50) relative to handle assembly (12) about longitudinal axis (LA) of guide catheter assembly (50), instead of thumbwheel (42) being operable to drive rotation of guide catheter assembly (50); and instead of knob (32) being operable to drive articulation of flexible guide shaft portion (54) as described below.

Articulation drive assembly (30) is configured to selectively drive articulation of flexible guide shaft portion (54) relative to longitudinal axis (LA) defined by guide catheter assembly (50). Articulation drive assembly (30) is operable to cause flexible guide shaft portion (54) to flex, to thereby deflect open distal tip (56) away from longitudinal axis (LA) of rigid guide shaft portion (52), as exemplified between FIGS. 3A-3B. Articulation drive assembly (30) includes a knob (32) that is coaxially disposed about rigid guide shaft portion (52) and a push-pull cable (34) (see FIGS. 3A-3B). Knob (32) is rotatable, relative to rigid guide shaft portion (52) and body portion (14), about longitudinal axis (LA) of rigid guide shaft portion (52), as indicated by arrow (4). Push-pull cable (34) may extend along a portion of flexible guide shaft portion (54) that is opposite of resilient spine (51). Push-pull cable (34) may be sufficiently spaced away from resilient spine (51) in order to flex resilient spine (51) in response to translation of push-pull cable (34). Push-pull cable (34) may be located exterior to, or within the confines of, internal lumen defined by flexible guide shaft portion (54).

Knob (32) is coupled with open distal tip (56) of flexible guide shaft portion (54) via push-pull cable (34) such that rotation of knob (32) about rigid guide shaft portion (52) causes translation of push-pull cable (34), thereby deflecting open distal tip (56), as exemplified between FIGS. 3A-3B. In particular, the operator may rotate knob (32) in a first rotational direction to actuate push-pull cable (34) proximally, thereby bending flexible guide shaft portion (54) such that open distal tip (56) is deflected from longitudinal axis (LA).

If the operator desires to straighten flexible guide shaft portion (54), the operator may rotate knob (32) in a second, opposite, rotational direction to actuate push-pull cable (34) distally, thereby allowing flexible guide shaft portion (54) to bend toward a non-articulated configuration due to the resilient nature of resilient spine (51). Articulation drive assembly (30) may be configured to deflect open distal tip (56) away from longitudinal axis (LA) to various angles in order to access various anatomical passageways as would be apparent to one skilled in the art in view of the teachings herein.

By way of further example only, articulation drive assembly (30) and flexible guide shaft portion (54) may be configured and operable in accordance with at least some of the teachings of U.S. Pat. Pub. No. 2019/0015645, entitled "Adjustable Instrument for Dilation of Anatomical Passageway," published Jan. 17, 2019, issued as U.S. Pat. No. 10,874,839 on Dec. 29, 2020, the disclosure of which is incorporated by reference herein; and/or U.S. Pat. Pub. No. 2018/0311472, entitled "Deflectable Guide for Medical Instrument," published Nov. 1, 2018, issued as U.S. Pat. No. 11,376,401 on Jul. 5, 2022, the disclosures of which are incorporated by reference herein.

As yet another merely illustrative example, instrument (10) may be configured such that thumbwheel (42) is operable to drive articulation of flexible guide shaft portion (54), instead of knob (32) being operable to drive rotation of guide catheter assembly (50) relative to handle assembly (12) about longitudinal axis (LA) of guide catheter assembly (50); and instead of thumbwheel (42) being operable to drive rotation of guide catheter assembly (50) relative to handle assembly (12) about longitudinal axis (LA) of guide catheter assembly (50).

B. Exemplary Guidewire Assembly and Dilation Catheter Assembly

As mentioned above, guidewire assembly (60) and dilation catheter assembly (70) are both slidably coupled to handle assembly (12) and guide catheter assembly (50) such that guidewire assembly (60) and dilation catheter assembly (70) may be independently actuated relative to guide catheter assembly (50) and each other. As will be described in greater detail below, guidewire assembly (60) and dilation catheter assembly (70) may be used in conjunction with handle assembly (12) and guide catheter assembly (50) in order to access and dilate a desired anatomical passageway.

As best seen in FIG. 2, guidewire assembly (60) includes a guidewire (62) and a guidewire movement mechanism (66). In some instances, guidewire (62) may include an optical fiber extending into a distal illuminating tip and/or position sensor. By way of example only, guidewire (62) may be configured in accordance with at least some of the teachings of U.S. Pat. No. 9,155,492, entitled "Sinus Illumination Lightwire Device," issued on Oct. 13, 2015; U.S. Pat. No. 9,757,018, entitled "Medical Guidewire with Integral Light Transmission," issued on Sep. 12, 2017; and/or U.S. Pat. No. 10,610,308, entitled "Navigation Guidewire with Interlocked Coils," issued on Apr. 7, 2020, the disclosures of which are incorporated by reference herein.

As mentioned above, guidewire movement mechanism (66) is slidably coupled to handle assembly (12) via first track (24) such that guidewire movement mechanism (66) may translate along first track (24) and through cavity (82) of dilation catheter movement mechanism (80). Guidewire (62) may be selectively coupled to guidewire movement mechanism (66) such that translation of guidewire movement mechanism (66) relative to handle assembly (12) drives translation of guidewire (62) in accordance with the description herein. Guidewire movement mechanism (66) includes a translating carriage (68) and a guidewire locking and rotation knob (67). Translating carriage (68) is slidably coupled to handle assembly (12) via first track (24), while guidewire locking and rotation knob (67) is rotatably disposed on translating carriage (68). In particular, guidewire locking and rotation knob (67) may rotate about its longitudinal axis relative to translating carriage (68); while knob (67) may also translate with carriage (68) relative to handle assembly (12).

Guidewire locking and rotation knob (67) is operatively coupled to guidewire (62) such that rotation of knob (67) about its own longitudinal axis drives rotation of guidewire (62) about its own longitudinal axis; and also such that translation of knob (67) relative to handle assembly (12) drives translation of guidewire (62). Knob (67) is secured to guidewire (62) such that knob (67) and guidewire (62) rotate unitarily. Therefore, if the operator rotates knob (67) relative to translating carriage (68) in a first rotational direction, the portion of guidewire (62) directly coupled to knob (67) rotates about its corresponding longitudinal axis in the first rotational direction, while the portion of guidewire (62) disposed within guidewire lumen (85) also rotates about its corresponding longitudinal axis in the first rotational direction, and distal end (64) of guidewire (62) also rotates about its corresponding longitudinal axis in the first rotational direction. Knob (67) may be configured for securely locking and unlocking guidewire (62) to guidewire movement mechanism (66), such that the longitudinal placement of guidewire (62) relative to dilation catheter (72) may be repositioned, or such that a new guidewire (62) may be used in replacement of a previously used guidewire (62).

As best seen in FIGS. 1-2, the portion of guidewire (62) extending distally from guidewire movement mechanism (66) extends into a skived slot (74) and a guidewire lumen (85) of dilation catheter (72). Guidewire (62) is slidably disposed within guidewire lumen (85) such that guidewire (62) may translate relative to dilation catheter (72), handle assembly (12), and guide catheter assembly (50). Therefore, a distal end (64) of guidewire (62) may translate distally and proximally through an open distal end (76) of dilation catheter (72). In some versions, the distal portion of guidewire (62) is more flexible than the proximal end of guidewire (62). In some versions, distal end (64) of guidewire (62) may be configured to illuminate, as such illumination may provide transcutaneous illumination through the patient's face to enable the operator to visually confirm positioning of the distal end (64) of guidewire (62) with relative ease. Various structures and methods to provide illumination to distal end (64) of guidewire (62) will be apparent to one skilled in the art in view of the teachings herein.

Skived slot (74) extends along dilation catheter (72) a suitable distance such that the portion of guidewire (62) extending between guidewire movement mechanism (66) and guidewire lumen (85) may translate during exemplary translation of guidewire (62), in accordance with the description herein, without being inhibited by dilation catheter (72). In other words, skived slot (74) is dimensioned to accommodate translation of guidewire assembly (60) relative to dilation catheter (72) during exemplary use in accordance with the description herein. Guidewire (62) has a length enabling distal end (64) of guidewire (62) to be suitably positioned distal to open distal end (76) of dilation catheter (72) while the proximal portion of guidewire (62) is suitably coupled to guidewire movement mechanism (66).

As best seen in FIG. 2, dilation catheter assembly (70) includes dilation catheter (72), an inflatable balloon (78), and dilation catheter movement mechanism (80) defining cavity (82). As mention above, dilation catheter movement mechanism (80) is slidably disposed on handle assembly (12) via second track (26) while a portion of dilation catheter (72) is slidably disposed within the portion of handle assembly (12) defining first track (24).

Dilation catheter (72) is coupled with dilation catheter movement mechanism (80) such that translation of dilation catheter movement mechanism (80) drives translation of dilation catheter (72) relative to handle assembly (12), dilation catheter assembly (70), and guidewire assembly (60). Additionally, a portion of dilation catheter (72) is slidably disposed within guide catheter assembly (50). Both guidewire (62) and dilation catheter (72) have a suitable length to enable distal end (64) of guidewire (62) and inflatable balloon (78) of dilation catheter assembly (70) to translate distally past open distal tip (56) of guide catheter assembly (50), while the proximal portions of guidewire (62) and dilation catheter (72) are suitably coupled to guidewire movement mechanism (66) and dilation catheter movement mechanism (80), respectively. A distal portion of dilation catheter (72) and/or inflatable balloon (78) may be suitably flexible in order to bend while sliding through flexible guide shaft portion (54) in a flexed position.

Inflatable balloon (78) is located at a distal portion of dilation catheter (72). Dilation catheter (72) defines guidewire lumen (not shown), an inflation lumen (now shown), and an irrigation lumen (not shown). Guidewire lumen (not shown) extends proximally into communication with skived slot (74) so that guidewire (62) may dive from guidewire movement mechanism (66) into guidewire lumen (not shown) via skived slot (74). Additionally, guidewire lumen (not shown) extends all the way to open distal end (76) of dilation catheter (72) such that distal end (64) of guidewire (62) may translate distally past open distal end (76) of dilation catheter (72). Inflation lumen (not shown) may be fluidly isolated from both guidewire lumen (not shown) and irrigation lumen (not shown). Inflation lumen (not shown) terminates distally within inflatable balloon (78). A proximal end of dilation catheter (72) comprises a first port (not shown) in fluid communication with inflation lumen (not shown) and a second port (not shown) in fluid communication with irrigation lumen (not shown).

Figure 5A:
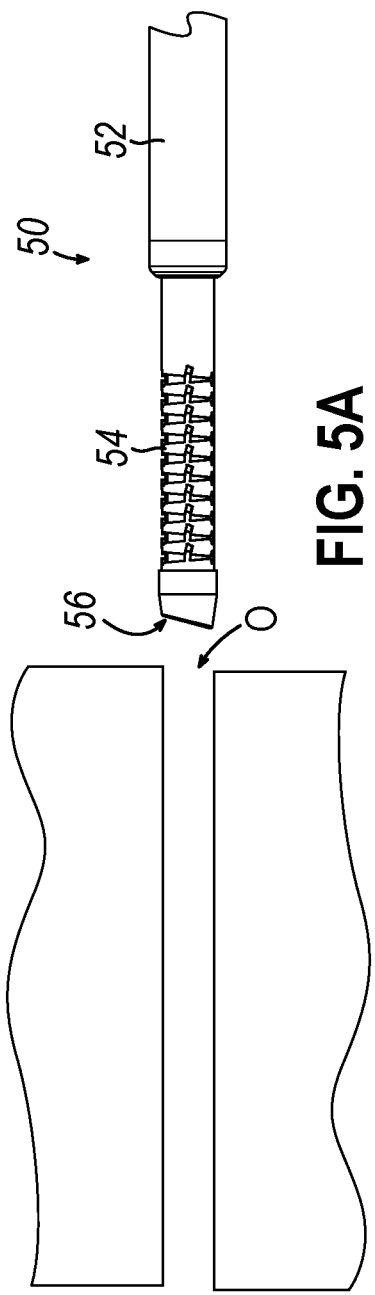
FIG. 5A depicts an elevational side view of an open distal tip of the guide catheter assembly of FIG. 1 placed adjacent to a sinus ostium of a patient, where a guidewire of the guidewire assembly of FIG. 1 is housed within the guide catheter assembly, and where an inflatable balloon of the dilation catheter assembly of FIG. 1 is housed within the guide catheter assembly in a deflated state.
Figure 5D:
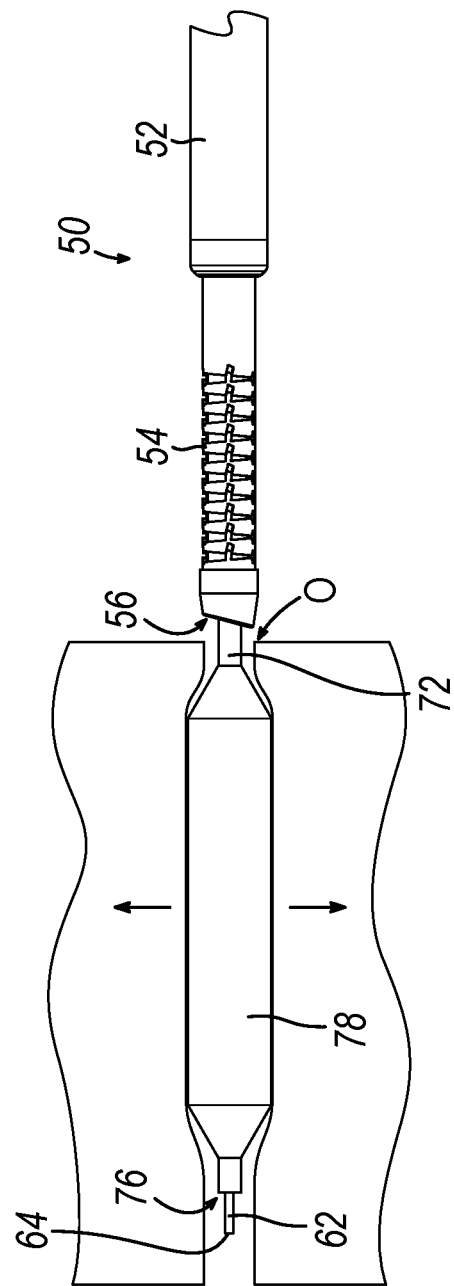
FIG. 5D depicts an elevational side view of the open distal tip of the guide catheter assembly of FIG. 1 placed adjacent to the sinus ostium of the patient, where a distal tip of the guidewire of FIG. 5A extends distally past the open distal tip of the guide catheter assembly, and where the inflatable balloon of the dilation catheter assembly of FIG. 1 extends distally past the open distal tip of the guide catheter assembly in an inflated state.

First port (not shown) may couple with an inflation device configured to communicate a sufficient amount of fluid to and from inflatable balloon (78) such that inflatable balloon (78) may transition between a deflated state (as shown in FIG. 5C) and an inflated state (as shown in FIG. 5D). Any suitable inflation device may be used as would be apparent to one skilled in the art in view of the teachings herein.

Irrigation lumen (not shown) may converge with guidewire lumen (not shown) distally along dilation catheter (72) such that irrigation lumen (not shown) and guidewire lumen (not shown) are in fluid communication with each other at the point of convergence and distally thereof. Second port (not shown) may couple with an irrigation device configured to communicate irrigation fluid through irrigation lumen (not shown) and out of open distal end (76) of dilation catheter (72). A portion of dilation catheter (72) extending distally from inflatable balloon (78) may have one or more circumferential openings for irrigation fluid to exit.

While in the current example, a dilation catheter (72) and inflatable balloon (78) is used as the working element, any other suitable catheter defining a guidewire lumen may be used as would be apparent to one skilled in the art in view of the teachings herein.

C. Exemplary Operation Using Instrument to Dilate Anatomical Passageway

FIGS. 4A-5D show an exemplary procedure to access and dilate a targeted anatomical passageway, such as a sinus ostium (O). While flexible guide shaft portion (54) is shown in a straight configuration in FIGS. 5A-5D, in actual use flexible guide shaft portion (54) may be flexed or bent to achieve a bend angle that facilitates access to a targeted anatomical passageway (e.g., maxillary sinus ostium, sphenoid sinus ostium, frontal recess, Eustachian tube, etc.). Flexible guide shaft portion (54) may be flexed or bent before guide catheter assembly (50) has been inserted into the patient and/or after guide catheter assembly (50) has been inserted into the patient. First, as best shown in FIG. 5A, open distal tip (56) of guide catheter assembly (50) may be first positioned near the targeted anatomical passageway, such as the sinus ostium (O) in this example. The positioning of open distal tip (56) of guide catheter assembly (50) may be performed under visualization provided by an endoscope.

Distal end (64) of guidewire (62) and inflatable balloon (78) and open distal end (76) of dilation catheter assembly (70) may be positioned within or proximal to flexible guide shaft portion (54) of guide catheter assembly (50) at this stage. FIG. 6A shows guidewire movement mechanism (66) and dilation catheter movement mechanism (80) located at corresponding proximal positions relative to handle assembly (12), where such proximal positions are associated with distal end (64) and open distal end (76) positioned within or proximal to flexible guide shaft portion (54) of guide catheter assembly (50).

Figure 4A:
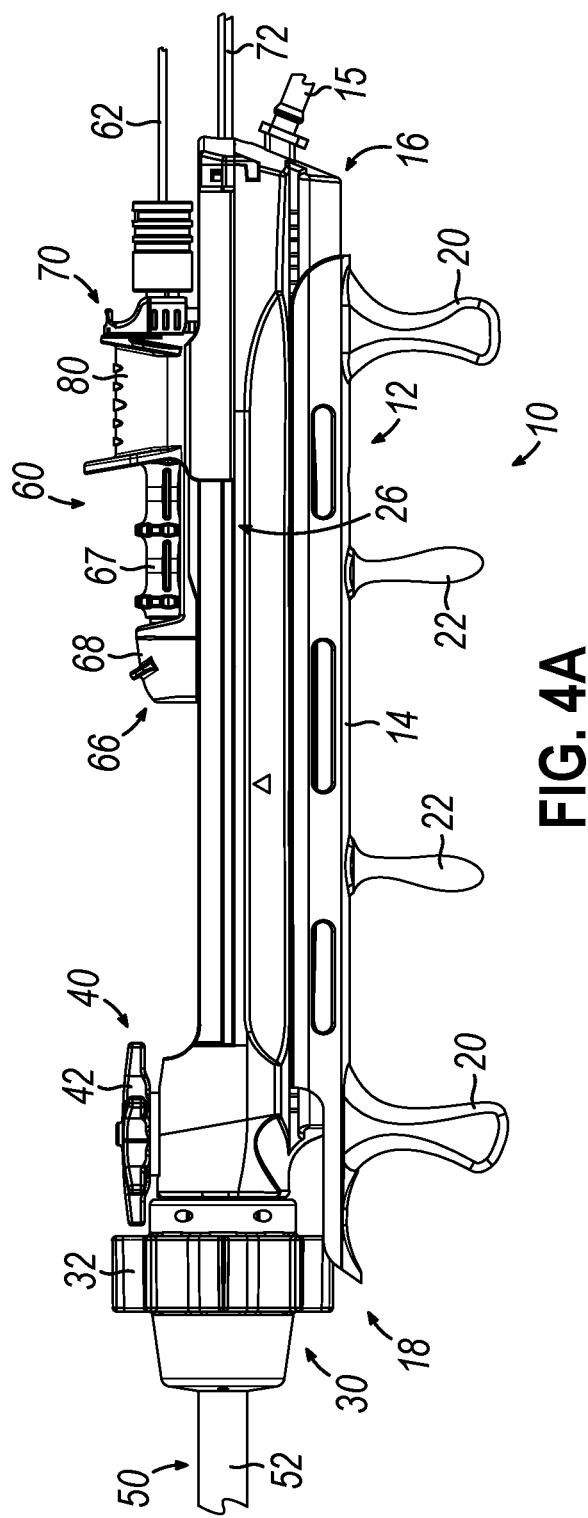
FIG. 4A depicts an elevational side view of the handle assembly of FIG. 1, where a guidewire movement mechanism of the guidewire assembly of FIG. 1 is in a proximal position, and where a dilation catheter movement mechanism of the dilation catheter assembly of FIG. 1 is in a proximal position.

After guide catheter assembly (50) has been positioned, the operator may advance guidewire movement mechanism (66) from the proximal position shown in FIG. 4A to a distal position shown in FIG. 4B. Distal movement of guidewire movement mechanism (66) drives guidewire (62) distally through open distal tip (56) of guide catheter assembly (50) such that a distal end (64) of guidewire (62) passes through the sinus ostium (O) (or some other targeted anatomical passageway), as shown in FIG. 5B. In instances where distal end (64) of guidewire (62) is configured to illuminate, the operator may illuminate distal end (64), which may provide transcutaneous illumination through the patient's face to enable the operator to visually confirm positioning of distal end (64) of guidewire (62) with relative ease.

With open distal tip (56) of guide catheter assembly (50) and guidewire (62) suitably positioned as shown in FIG. 5B, the operator may advance dilation catheter movement mechanism (80) from the proximal position shown in FIG. 4B to a distal position shown in FIG. 4C. Distal movement of dilation catheter movement mechanism (80) drives inflatable balloon (78) along guidewire (62) and through open distal tip (56) of guide catheter assembly (50) with inflatable balloon (78) in the deflated state such that inflatable balloon (78) is positioned through the sinus ostium (O) (or some other targeted anatomical passageway), as shown in FIG. 5C.

After inflatable balloon (78) has been positioned within the ostium (O), inflatable balloon (78) may be inflated as shown in FIG. 5D, thereby dilating the ostium (O). Balloon (78) may be inflated utilizing any suitable technique as would be apparent to one skilled in the art in view of the teachings herein. By way of example only, inflatable balloon (78) may be inflated to a pressure of about 10 to about 12 atmospheres. Inflatable balloon (78) may be held at this volume for a few seconds to sufficiently open the ostium (O) (or other targeted anatomical passageway). Inflatable balloon (78) may then be returned to a deflated state utilizing any suitable technique as would be apparent to one skilled in the art in view of the teachings herein. Inflatable balloon (78) may be repeatedly inflated and deflated in different ostia and/or other targeted anatomical passageways.

Thereafter, guidewire movement mechanism (66) and dilation catheter movement mechanism (80) may be moved back to their respective proximal positions, thereby proximally translating guidewire (62) and dilation catheter (72) back into guide catheter assembly (50). Guide catheter assembly (50) may be then removed from the patient.

It should be understood that irrigation and/or suction may be provided during any suitable portion of the procedure. Irrigation and/or suction may be provided in accordance with description herein or utilizing other suitable methods and/or devices as would be apparent to one skilled in the art in view of the teachings herein. dilation catheter assembly (70), guidewire assembly (60), and guide catheter assembly (50) may be removed from the patient.

II. Exemplary Flexible Guide Shaft Portion with Partial Sleeve

As mentioned above, fluid lumen (15) is in fluid communication with an internal lumen of guide catheter assembly (50) via an internal passageway (not shown) defined by body portion (14) such that suction/irrigation source (17) (see FIG. 1) may provide suction/irrigation at open distal tip (56) of guide catheter assembly (50) during exemplary use. However, as also mentioned above, adjacent flexing bodies

(58) of flexible guide shaft portion (54) define respective gaps (59) in order to accommodate for further flexing of bodies (58).

Gaps (59) may provide fluid communication between interior lumen and an exterior of flexible guide shaft portion (54) such that fluid/suction intended to communicate with open distal tip (56) may prematurely escape through gaps (59) instead of suitably reaching open distal tip (56). Therefore, in some instances, it may be desirable to provide a sleeve that at least partially covers gaps (59) in an attempt to inhibit fluid/suction from escaping via gaps (59), thereby allowing the intended fluid/suction to suitably travel through open distal tip (56) instead of gaps (59), while also accommodating for the flexing of flexible guide shaft portion (54) in accordance with the description herein.

Additionally, as mentioned above, inflatable balloon (78) and open distal end (76) of dilation catheter assembly (70) may be positioned within or proximal to flexible guide shaft portion (54) of guide catheter assembly (50) such that inflatable balloon (78) may translate within flexible guide shaft portion (54). As also mentioned above, when flexing bodies (58) move toward and away from each other in order to articulate open distal tip (56) in accordance with the description herein, the size of gaps (59) change, and in some instances, gaps (59) are actually closed.

In some instances, inflatable balloon (78) may tend to snag or otherwise undesirably contact portions of flexible bodies (58) defining gaps (59) during advancement and/or retraction of inflatable balloon (78) within the internal lumen. If inflatable balloon (78) (or any other suitable device) is housed within flexible guide shaft portion (54) while flexible bodies (58) move toward each other in order to articulate open distal tip (56) in accordance with the description herein, the portions of flexible bodies (58) defining gaps (59) may undesirably capture and/or pinch inflatable balloon (78) (or any other suitable device), which may in turn damage inflatable balloon (78) (or any other suitable device). Therefore, in some instances, it may be desirable to provide a sleeve that at least partially protects inflatable balloon (78) (or any other suitable device) from being pinched, captured, or damaged by flexing bodies (58) while open distal tip (56) is articulating or while inflatable balloon (78) is translating within internal lumen defined by flexible guide shaft portion (54).

Figure 6:
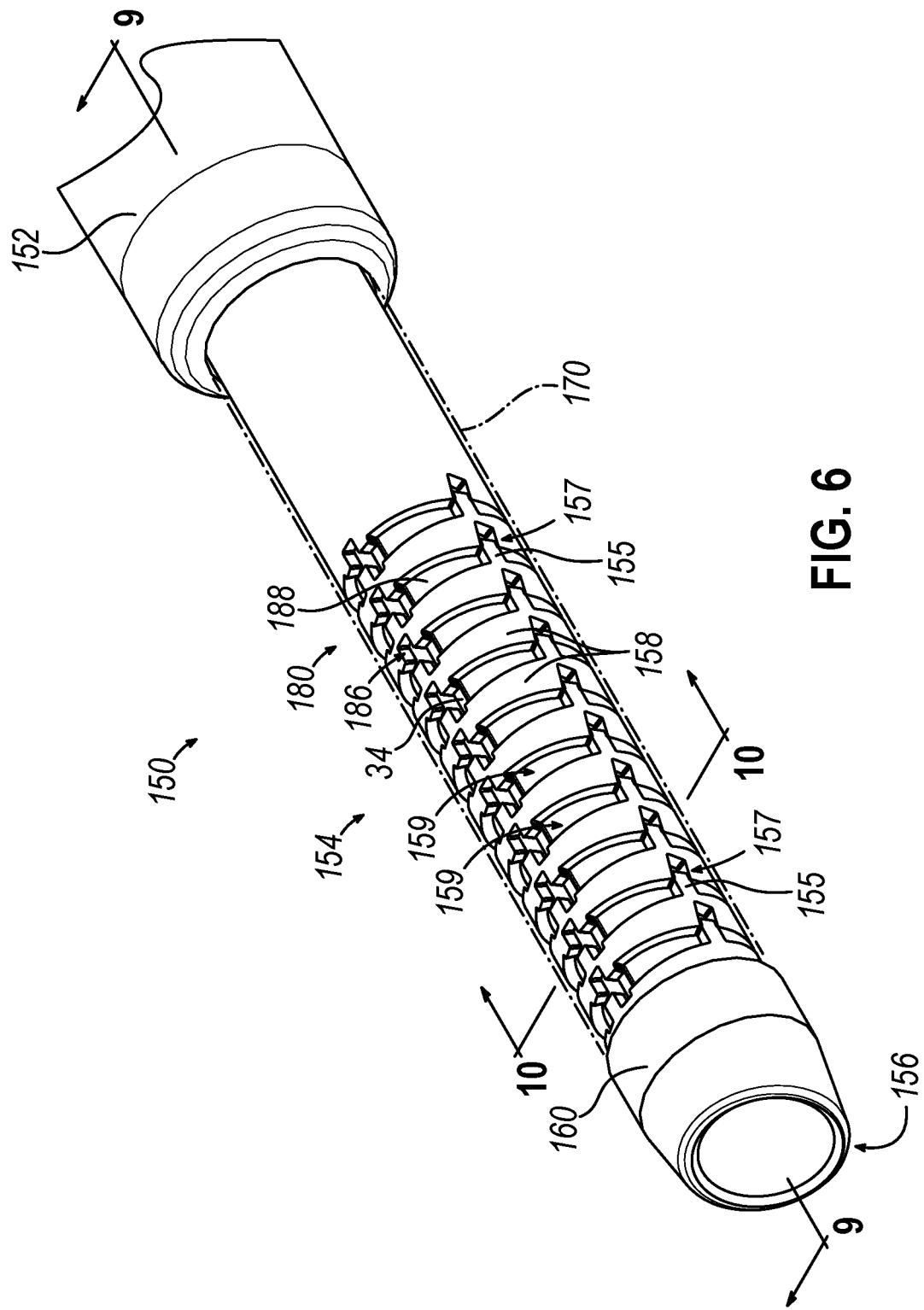
FIG. 6 depicts a perspective view of an alternative guide catheter assembly that may be readily incorporated into the instrument of FIG. 1.
Figure 7:
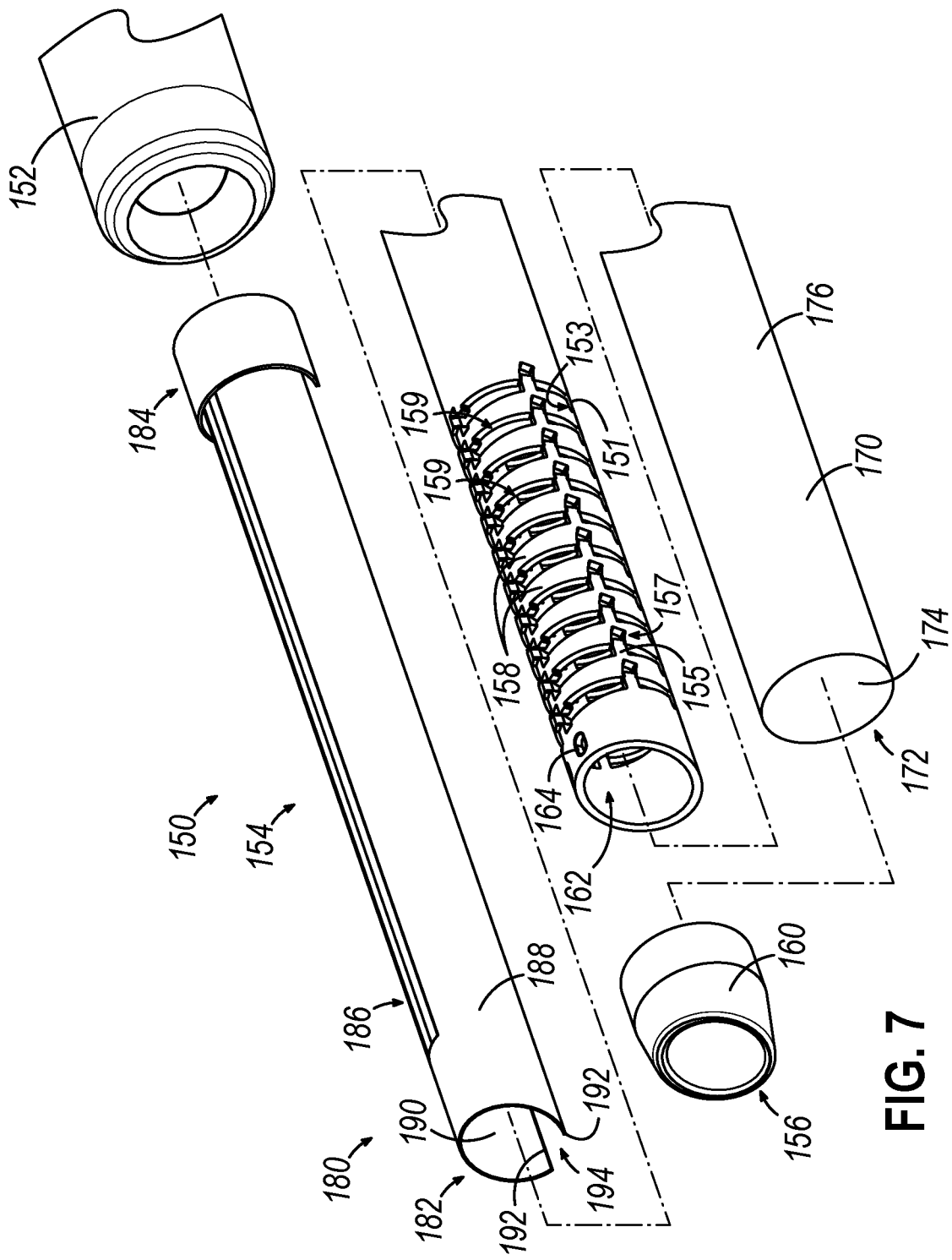
FIG. 7 depicts an exploded perspective view of the guide catheter assembly of FIG. 6.
Figure 8:
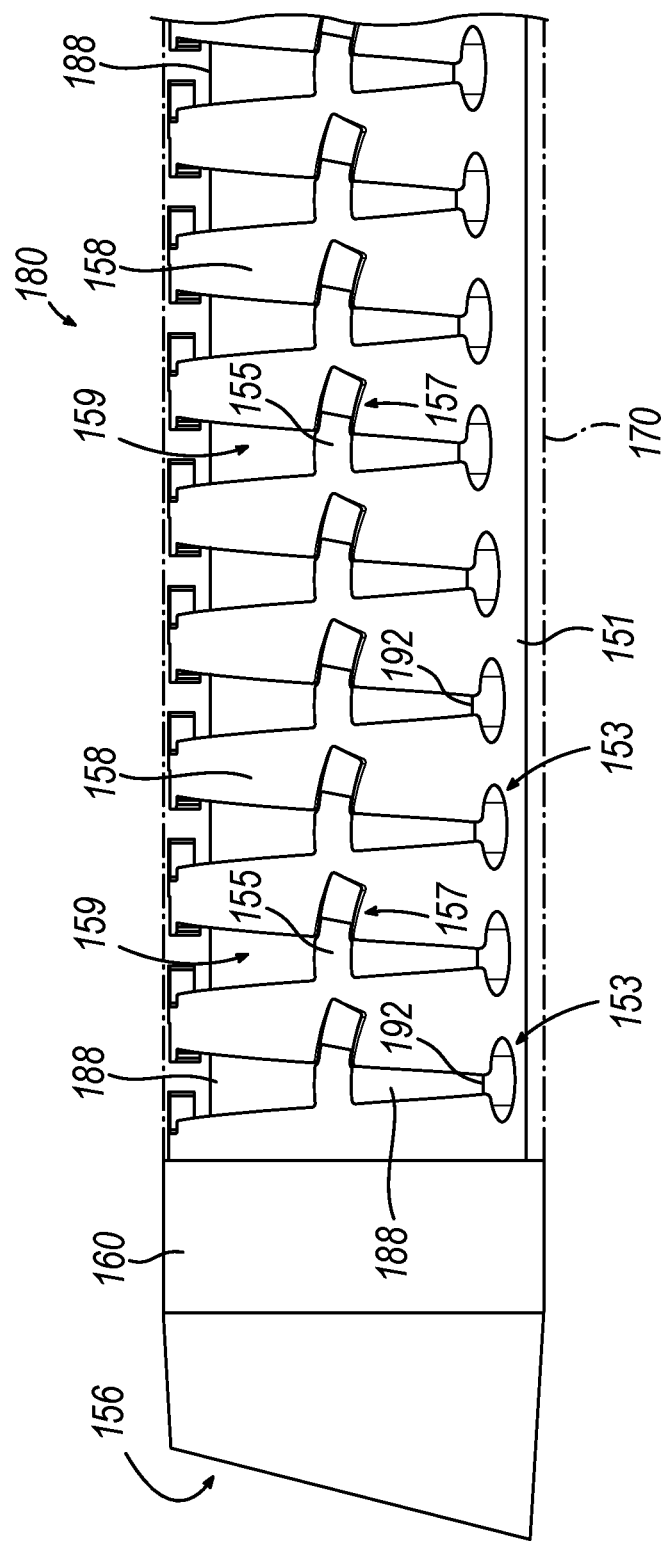
FIG. 8 depicts an elevational side view of the guide catheter assembly of FIG. 6.

FIGS. 6-8 show an alternative guide catheter assembly (150) that may be readily incorporated into instrument (10) in replacement of guide catheter assembly (50) described above. Guide catheter assembly (150) may be substantially similar to guide catheter assembly (50) described above, with differences elaborated below. Like guide catheter assembly (50), guide catheter assembly (150) includes a rigid guide shaft portion (152) and a flexible guide shaft portion (154) that are substantially similar to rigid guide shaft portion (52) and flexible guide shaft portion (54) described above. Rigid guide shaft portion (152) may be operatively coupled with rotation drive assembly (40) of handle assembly (12) such that rotation drive assembly (40) may rotate guide catheter assembly (150) about longitudinal axis (LA). Additionally, flexible guide shaft portion (154) may be operatively coupled to articulation drive assembly (30) of handle assembly (12) such that articulation drive assembly (30) may flex flexible guide shaft portion (154) in accordance with the description herein.

Flexible guide shaft portion (154) includes a longitudinally extending resilient spine (151) and a linear array of flexing bodies (158) having complementary interlocking features (155, 157) which are substantially similar to resilient spine (51), flexing bodies (58), and complementary interlocking features (155, 157) described above, with differences elaborated below. Therefore, flexible bodies (158) define a plurality of gaps (159), which are substantially similar to gaps (59) described above. As best seen in FIG. 7, resilient spine (151) and flexing bodies (158) define an internal lumen (162) that is in communication with an internal lumen of rigid guide shaft portion (152) and open distal tip (156). In the current example, flexible guide shaft portion (154) includes a tip body (160) defining open distal tip (156). Tip body (160) is coupled with the most distal flexible body (158).

Figure 9:
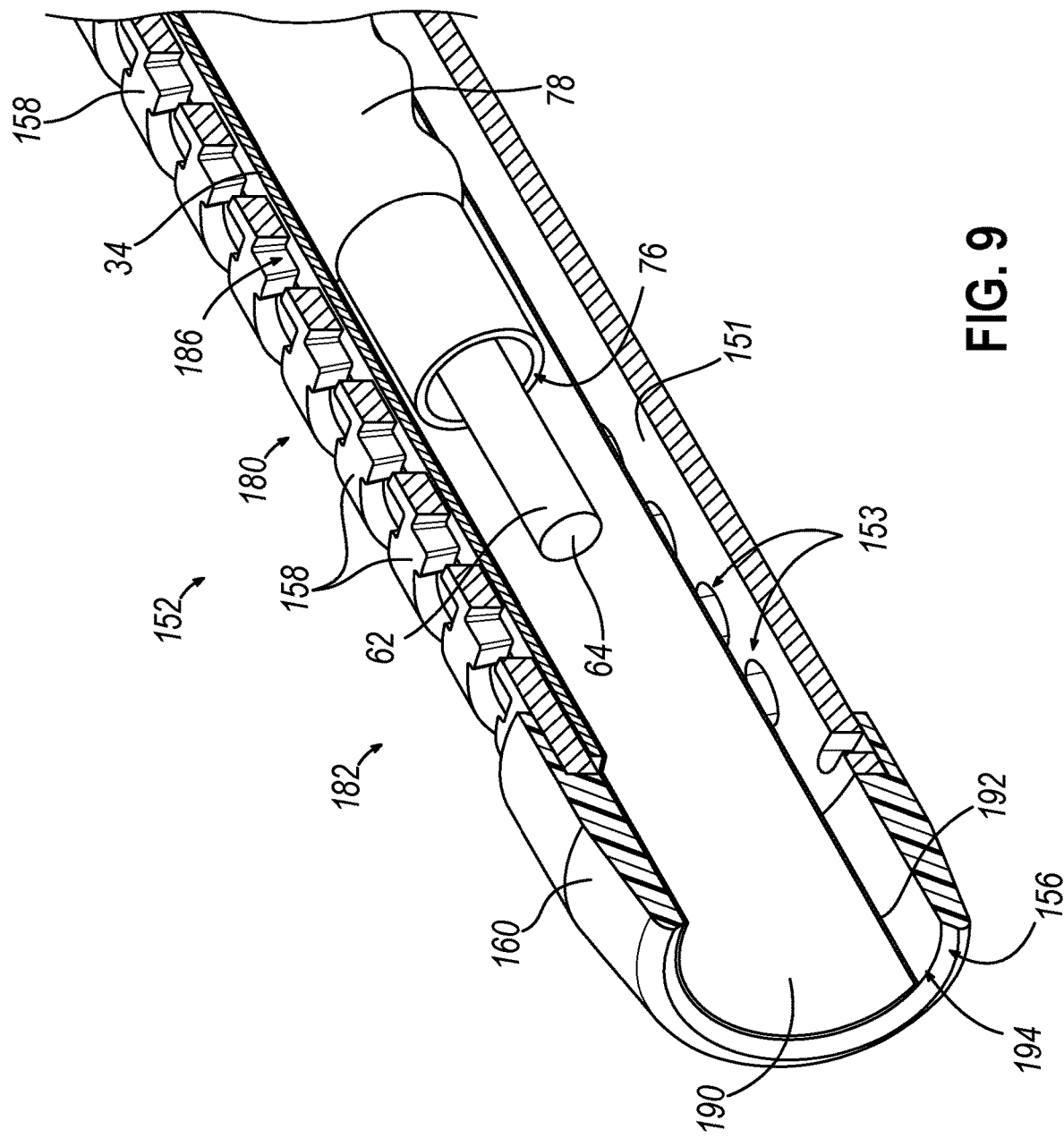
FIG. 9 depicts a sectional view of the guide catheter assembly of FIG. 6, taken along line 9-9 of FIG. 6.

The most distal flexing body (158) defines at least one coupling feature (164) that may couple with push-pull cable (34) of articulation drive assembly (30) when assembled. As best shown in FIG. 9, push-pull cable (34) may extend along an interior portion of flexing bodies (158) in order to couple with coupling feature (164). Push-pull cable (34) may be soldered, laser welded, or coupled to coupling feature (164) utilizing any other suitable means as would be apparent to one skilled in the art in view of the teachings herein. As best seen in FIG. 8, resilient spine (151) defines a plurality of flexing cutouts (153), from which flexing bodies (158) extend. Flexing cutouts (153) may promote flexing of bodies (158) during articulation of open distal tip (156).

As best seen in FIG. 7, flexible guide shaft portion (154) also includes an outer sleeve or liner (170) and a partial interior sleeve or liner (180). As will be described in greater detail below, outer sleeve (170) is disposed around an exterior of resilient spine (151) and linear array of flexing bodies (158) defining gaps (159) in order to inhibit fluid from escaping via gaps (159), thereby promoting suitable fluid communication between suction/irrigation source (17) and open distal tip (156). Additionally, as will be described in greater detail below, partial interior sleeve (180) is disposed within an interior of resilient spine (151) and array of flexing bodies (158) defining gaps (159) in order to both protect working elements slidably disposed within an internal lumen (162) defined by resilient spine (151) and flexible bodies (158), as well as to promote suitable fluid communication between suction/irrigation source (17) and open distal tip (156).

Outer sleeve (170) extends from an interior portion of rigid guide shaft portion (152) all the way to tip body (160). Outer sleeve (170) includes an interior surface (174) and an exterior surface (176). Interior surface (174) defines a channel (172) dimensioned to house resilient spine (151) and flexing bodies (158). In the current example, outer sleeve (170) forms a completed annular shape such that interior surface (174) and exterior surface (176) are both continuous circumferentially. However, this is merely optional, as interior surface (174) and exterior surface (176) may terminate at longitudinally extending edges, such that interior surface (174) suitably covers gaps (159) and flexing cutouts (153), similar to that of partial internal sleeve (180) described below.

Outer sleeve (170) is formed from a suitably flexible material such that outer sleeve (170) may flex along with flexing bodies (158) in order to accommodate articulation of open distal tip (156) in accordance with the description above. Additionally, terminating ends of outer sleeve (170) are coupled with respective rigid guide shaft portion (152) and tip body (160) to provide a fluid tight seal within channel (172). Therefore, outer sleeve (170) sufficiently covers gaps (159) and flexing cutouts (153) in order to prevent air/fluid from escaping out of gaps (159) and flexing cutouts (153). Outer sleeve (170) may conform to the profile of flexing bodies (158) while also inhibiting fluid from escaping via gaps (159), thereby promoting suitable fluid communication between suction/irrigation source (17) and open distal tip (156).

Figure 10:
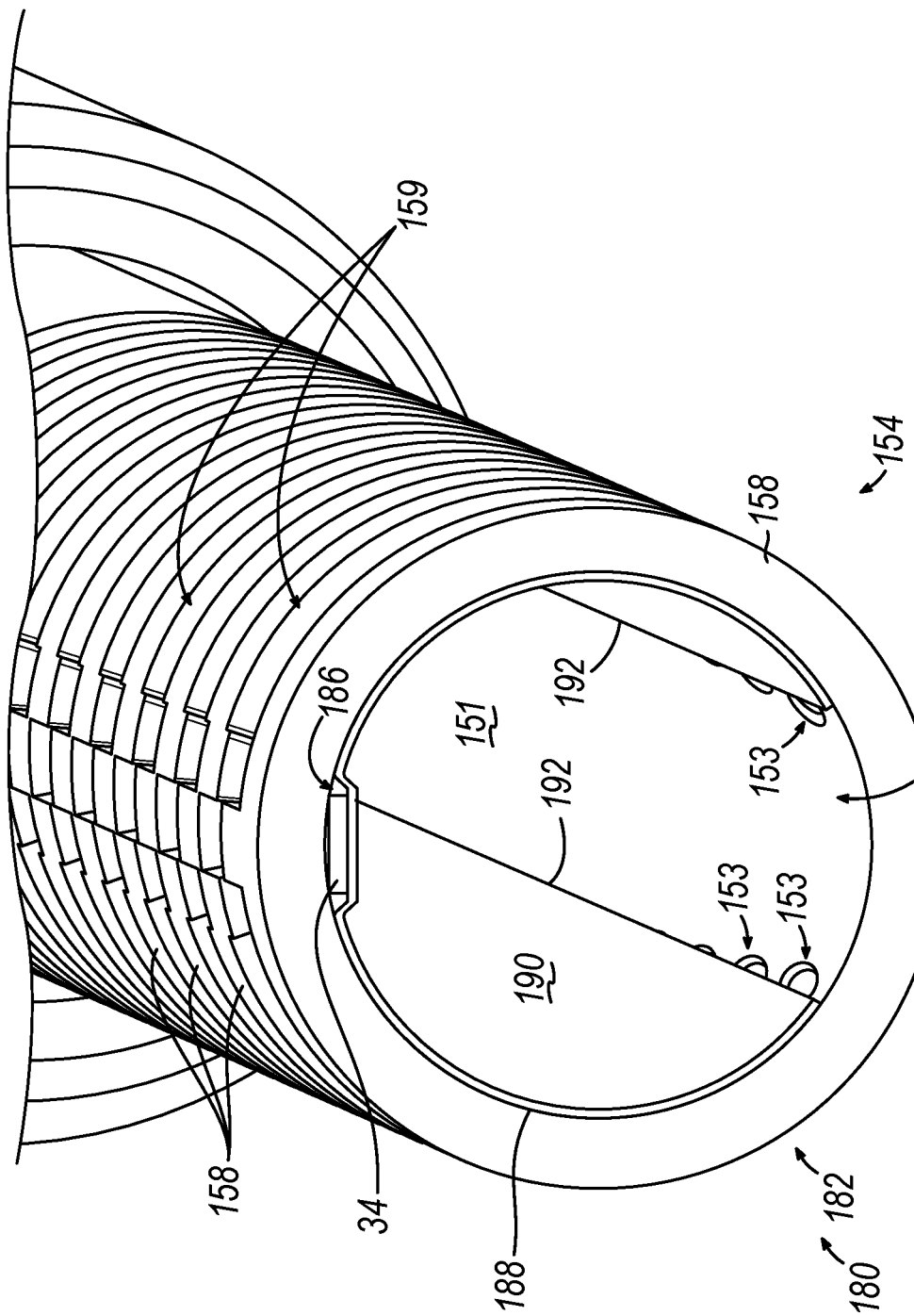
FIG. 10 depicts a sectional view of the guide catheter assembly of FIG. 6, taken along line 10-10 of FIG. 6.
Figure 11:
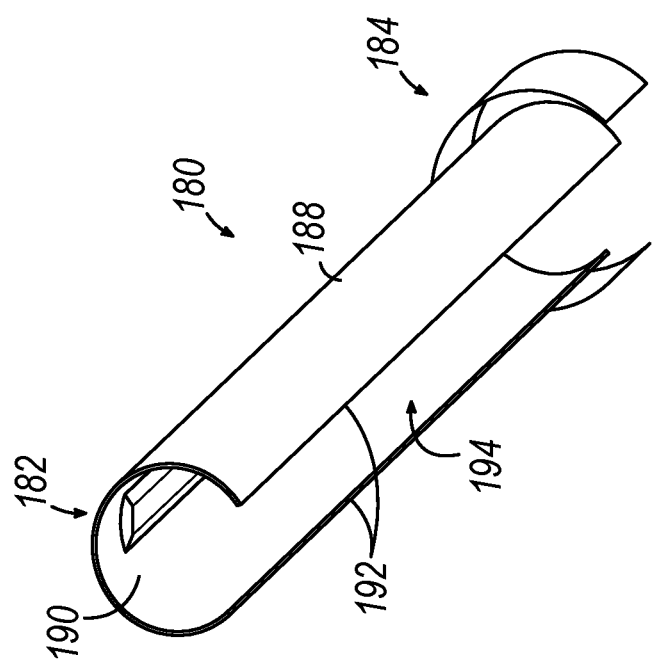
FIG. 11 depicts a perspective view of a partial interior sleeve of the guide catheter assembly of FIG. 6.

Partial interior sleeve (180) extends between a distal portion (182) and a proximal portion (184). Partial interior sleeve (180) includes an exterior surface (188) defining a longitudinally extending push-pull cable recess (186), and an interior surface (190). Interior surface (190) and exterior surface (188) extend angularly between longitudinally extending sleeve edges (192), which together define a longitudinally extending gap (194) (as best seen in FIG. 11). In other words, interior surface (190) and exterior surface (188) do not extend angularly in a continuous fashion throughout a full 360 degree angular range, as outer sleeve (170) does; but instead terminate into longitudinally extending sleeve edges (192). Yet in other words, as best seen in FIG. 10, partial interior sleeve (180) has a crescent shape or a "C"-shape. Surfaces (188, 190) may extend any suitable angular distance in order to define any suitably sized gap (194) as would be apparent to one skilled in the art in view of the teachings herein. In some instances, partial interior sleeve (180) may only cover a portion of the interior surfaces flexing bodies (158) such that gaps (159) are partially exposed.

Partial interior sleeve (180) is housed within the interior of tip body (160) as well as internal lumen (162) such that external surface (188) is in suitable contact with the interior surface of tip body (160), as well as the interior surfaces of flexing bodies (158). Exterior surface (188) may be sufficiently coupled with interior surface of tip body (160) and/or interior surfaces of flexing bodies (158) through any suitable means as would be apparent to one skilled in the art in view of the teachings herein, such as gluing, etc. In some instances, partial interior sleeve (180) is not coupled to tip body (160) or flexing bodies (158).

Figure 12:
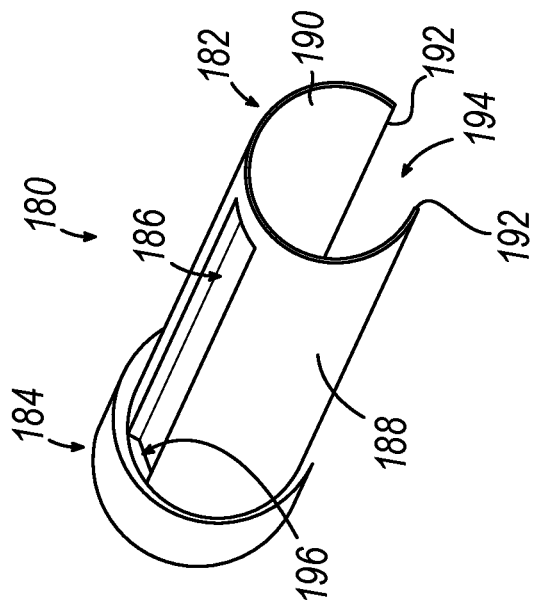
FIG. 12 depicts another perspective view of the partial interior sleeve of FIG. 11.

As best seen in FIGS. 9-10, push-pull cable recess (186) is dimensioned to house push-pull cable (34) such that push-pull cable (34) may be interposed between exterior surface (188) of partial interior sleeve (180) and the interior surface of flexing bodies (158). As best seen in FIG. 12, proximal portion (184) of partial interior sleeve (180) defines a through hole (196) in order to accommodate push-pull cable (34) to extend proximally toward handle assembly (12) in accordance with the description herein. In some instances, a liner material may be interposed between push-pull cable (34) and push-pull cable recess (186). In some instances, a pre-formed recess within exterior surface (188) does not exist, such that a recess initially forms when push-pull cable (34) is interposed between interior sleeve (180) and interior surface of flexing bodies (158).

Push-pull cable (34) may be glued to adjacent portions of push-pull cable recess (186) or liner material. However, push-pull cable (34) may be coupled with adjacent portions of push-pull cable recess (186) or liner material using any suitable means as would be apparent to one skilled in the art in view of the teachings herein. Gluing or otherwise coupling push-pull cable (34) with exterior surface (188) of interior sleeve (180) may inhibit interior sleeve (180) from warping, or otherwise deforming, due to flexible guide shaft portion (154) transitioning between an articulated position (as demonstrated in FIG. 3B) and a non-articulated position (as demonstrated in FIG. 3A).

As best seen in FIGS. 9-10, longitudinally extending sleeve edges (192) are longitudinally disposed within internal lumen (162) such that sleeve edges (192) are adjacent to flexing cutouts (153). Additionally, sleeve edges (192) are laterally spaced from resilient spine (151) such that longitudinally extending gap (194) extends directly adjacent to resilient spine (151).

Terminating ends of partial interior sleeve (180), including sleeve edges (192), may be suitably coupled with respective portions of internal lumen (162), rigid guide shaft portion (152), and tip body (160), in order to sufficiently inhibit an undesirable amount of fluid communication between internal lumen (162) and gaps (159) and/or flexing cutouts (153). Therefore, partial interior sleeve (180) may sufficiently cover gaps (159) and flexing cutouts (153) in order to prevent an undesirable amount of air/fluid from escaping out of gaps (159) and flexing cutouts (153). Partial interior sleeve (180) may conform to the profile of flexing bodies (158) while also inhibiting fluid from escaping via gaps (159), thereby promoting suitable fluid communication between suction/irrigation source (17) and open distal tip (156). In some instances, partial interior sleeve (180) may prevent a sufficient amount of air/fluid from escaping, such that outer sleeve (170) may be omitted. Yet in other instances, partial interior sleeve (180) and outer sleeve (170) may cooperate together in order to prevent a sufficient amount of air/fluid form escaping. Yet in other instances, partial interior sleeve (180) may not be configured to prevent an undesirable amount of air/fluid from escaping such that outer sleeve (170) prevents a suitable amount of air/fluid from escaping.

Partial interior sleeve (180) is formed from a suitably flexible material such that partial interior sleeve (180) may flex along with flexing bodies (158) in order to accommodate articulation of open distal tip (156) in accordance with the description above. As best shown in FIG. 10, longitudinally extending gap (194) extends laterally a suitable distance such that as flexing bodies (158) bend toward an articulated configuration, partial interior sleeve (180) does not collapse upon itself within internal lumen (162) when guidewire (62) and inflatable balloon (78) are proximally removed from flexible guide shaft portion (154). If partial interior sleeve (180) collapsed upon itself within internal lumen (162) while in the articulated configuration, fluid communication between open distal tip (56) and suction/irrigation source (17) may be undesirably interrupted/blocked. The chance of an interior sleeve (180) housed within internal lumen (162) collapsing upon itself may be greater if interior sleeve (180) extends angularly in a continuous fashion (like external sleeve (170)), or if gap (194) is not suitably wide enough. Therefore, since interior sleeve (180) does not extend angularly in a continuous fashion, partial interior sleeve (180) may be inhibited from collapsing upon itself while in the articulated configuration.

As best seen in FIG. 9, interior surface (190) of sleeve (180) is positioned within internal lumen (162) in order to protect inflatable balloon (78) from snagging or contacting portions of flexible bodies (158) defining gaps (159) during advancement and/or retraction of inflatable balloon (78), as well as protecting inflatable balloon (78) from being pinched by portions of flexing bodies (158) defining gaps (159) during articulation of open distal tip (156). Therefore, partial interior sleeve (180) may protect inflatable balloon (78) from undesirable damage, while also allowing suction/irrigation source (17) to provide suction/irrigation at open distal tip (56) of guide catheter assembly (50) in the articulated configuration during exemplary use in accordance with the description herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A catheter system comprising: (a) a body; (b) a guide member assembly extending distally from the body, wherein the guide member assembly comprises: (i) a proximal rigid portion defining a longitudinal axis, (ii) a distal flexible portion, and (iii) an open distal end, wherein the guide member assembly defines a lumen, wherein the lumen is in communication between the body and the open distal end; (c) an articulation assembly operatively coupled to the distal flexible portion, wherein the articulation assembly is configured to flex the distal flexible portion and the open distal end relative to the longitudinal axis between a straight configuration and an articulated configuration; and (d) a partial sleeve disposed within a portion of the lumen defined by the distal flexible portion, wherein the partial sleeve defines a longitudinally extending gap.

Example 2

The catheter system of Example 1, wherein the partial sleeve comprises a crescent shape.

Example 3

The catheter system of any one or more of Examples 1 through 2, wherein the distal flexible portion comprises a resilient spine.

Example 4

The catheter system of Example 3, wherein the longitudinally extending gap is directly adjacent to the resilient spine.

Example 5

The catheter system of any one or more of Examples 1 through 4, wherein the distally flexible portion comprises an array of flexible bodies, wherein adjacent flexible bodies define an adjustable gap configured to change dimensions in response to the distal flexible portion flexing between the straight configuration and the articulated configuration.

Example 6

The catheter system of Example 5, wherein the partial sleeve covers the adjustable gaps defined by the flexible bodies.

Example 7

The catheter system of Example 6, further comprising a working element slidably disposed within the lumen.

Example 8

The catheter system of Example 7, wherein the working element further comprises an inflatable balloon.

Example 9

The catheter system of Example 8, wherein the internal sleeve is configured and positioned to shield the inflatable balloon from the adjustable gaps defined by the flexible bodies.

Example 10

The catheter system of any one or more of Examples 1 through 9, further comprising a suction source or an irrigation source in fluid communication with the open distal tip of the guide member assembly.

Example 11

The catheter system of Example 10, wherein the distal flexible portion defines a plurality of adjustable gaps, wherein the partial sleeve sufficiently covers the adjustable gaps to promote fluid communication between the open distal tip and the suction source or the irrigation source.

Example 12

The catheter system of any one or more of Examples 1 through 11, wherein the articulation assembly comprises a push-pull cable.

Example 13

The catheter system of Example 12, wherein the partial sleeve defines a longitudinally extending recess housing the push-pull cable.

Example 14

The catheter system of Example 13, wherein the push-pull cable is interposed between the longitudinally extending recess and an internal surface of the distal flexible portion.

Example 15

The catheter system of Example 14, further comprising a liner disposed between the push-pull cable and the longitudinally extending recess.

Example 16

The catheter system of any one or more of Examples 12 through 15, wherein the push-pull cable is coupled with the partial sleeve.

Example 17

The catheter system of any one or more of Examples 1 through 16, further comprising an exterior sleeve disposed on an exterior of the distal flexible portion.

Example 18

A catheter system comprising: (a) a body; (b) a guide member assembly extending distally from the body, wherein the guide member assembly comprises: (i) a proximal rigid portion defining a longitudinal axis, (ii) a distal flexible portion comprising a longitudinally extending resilient spine and a plurality of flexing bodies defining a plurality of adjustable gaps, and (iii) an open distal end, wherein the guide member assembly defines a lumen, wherein the lumen is in communication between the body and the open distal end; (c) an articulation assembly operatively coupled to the distal flexible portion, wherein the articulation assembly is configured to flex the distal flexible portion and the open distal end relative to the longitudinal axis between a straight configuration and an articulated configuration; and (d) a partial sleeve disposed within a portion of the lumen defined by the distal flexible portion, wherein the partial sleeve defines a longitudinally extending gap extending adjacent to the longitudinally extending resilient spine.

Example 19

The catheter system of Example 18, wherein the partial sleeve covers the plurality of adjustable gaps.

Example 20

A catheter system comprising: (a) a body; (b) a guide member assembly extending distally from the body, wherein the guide member assembly comprises: (i) a proximal rigid portion defining a longitudinal axis, (ii) a distal flexible portion configured to flex the distal flexible portion and the open distal end relative to the longitudinal axis between a straight configuration and an articulated configuration, wherein the distal flexible portion defines a plurality of gaps in the straight configuration, and (iii) an open distal end, wherein the guide member assembly defines a lumen, wherein the lumen is in communication between the body and the open distal end; (c) a partial sleeve disposed within the distal flexible portion, wherein the partial sleeve defines a longitudinally extending gap, wherein the partial sleeve covers the plurality of gaps in the straight configuration.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A catheter system comprising:
    (a) a body;
    (b) a guide member assembly extending distally from the body, wherein the guide member assembly comprising:
        (i) a proximal rigid portion defining a longitudinal axis,
        (ii) a distal flexible portion defining a plurality of adjustable gaps, and
        (iii) an open distal end, the guide member assembly defining a lumen, the lumen being in communication between the body and the open distal end;
(c) an articulation assembly operatively coupled to the distal flexible portion, the articulation assembly being configured to flex the distal flexible portion and the open distal end relative to the longitudinal axis between a straight configuration and an articulated configuration; and
(d) a partial sleeve disposed within a portion of the lumen defined by the distal flexible portion, the partial sleeve comprising a pair of longitudinally extending edges together defining a longitudinally extending gap, the gap being laterally interposed between the longitudinally extending edges; and
(e) a suction source or an irrigation source in fluid communication with the open distal tip of the guide member assembly, wherein the partial sleeve sufficiently covers the adjustable gaps to promote fluid communication between the open distal tip and the suction source or the irrigation source.

2. The catheter system of claim 1, the partial sleeve comprising a crescent shape.

3. The catheter system of claim 1, the distal flexible portion comprising a resilient spine.

4. The catheter system of claim 3, the longitudinally extending gap being directly adjacent to the resilient spine.

5. The catheter system of claim 1, the distal flexible portion comprising an array of flexible bodies, adjacent flexible bodies defining the plurality of adjustable gaps configured to change dimensions in response to the distal flexible portion flexing between the straight configuration and the articulated configuration.

6. The catheter system of claim 5, the partial sleeve covering the plurality of adjustable gaps defined by the flexible bodies.

7. The catheter system of claim 6, further comprising a working element slidably disposed within the lumen.

8. The catheter system of claim 7, the working element further comprising an inflatable balloon.

9. The catheter system of claim 8, the partial sleeve being configured and positioned to shield the inflatable balloon from the adjustable gaps defined by the flexible bodies.

10. The catheter system of claim 1, the articulation assembly comprising a push-pull cable.

11. The catheter system of claim 10, the partial sleeve defining a longitudinally extending recess housing the push-pull cable.

12. The catheter system of claim 11, the push-pull cable being interposed between the longitudinally extending recess and an internal surface of the distal flexible portion.

13. The catheter system of claim 10, the push-pull cable being coupled with the partial sleeve.

14. The catheter system of claim 1, further comprising an exterior sleeve disposed on an exterior of the distal flexible portion.

15. A catheter system comprising:
(a) a body;
(b) a guide member assembly extending distally from the body, the guide member assembly comprising:
(i) a proximal rigid portion defining a longitudinal axis,
(ii) a distal flexible portion comprising a longitudinally extending resilient spine and a plurality of flexing bodies defining a plurality of adjustable gaps, and
(iii) an open distal end,
the guide member assembly defining a lumen, the lumen being in communication between the body and the open distal end;
(c) an articulation assembly operatively coupled to the distal flexible portion, the articulation assembly being configured to flex the distal flexible portion and the open distal end relative to the longitudinal axis between a straight configuration and an articulated configuration; and
(d) a partial sleeve covering the plurality of adjustable gaps disposed within a portion of the lumen defined by the distal flexible portion, the partial sleeve defining a crescent shape as viewed from a longitudinal end of the partial sleeve, the crescent shape being bound by a pair of longitudinally extending edges, the pair of longitudinally extending edges defining a longitudinally extending gap extending adjacent to the longitudinally extending resilient spine.

16. A catheter system comprising:
(a) a body;
(b) a guide member assembly extending distally from the body, the guide member assembly comprising:
(i) a proximal rigid portion defining a longitudinal axis,
(ii) a distal flexible portion configured to flex the distal flexible portion relative to the longitudinal axis between a straight configuration and an articulated configuration, the distal flexible portion defining a plurality of gaps in the straight configuration, and
(iii) an open distal end, the guide member assembly defining a lumen, the lumen being in communication between the body and the open distal end;
(c) a partial sleeve disposed within the distal flexible portion, the partial sleeve defining a C-shape as viewed from a longitudinal end of the partial sleeve, the C-shape defining a longitudinally extending gap, the partial sleeve covering the plurality of gaps in the straight configuration;
(d) an inflatable balloon slidably disposed within the lumen, wherein the partial sleeve is configured and positioned to shield the inflatable balloon from the adjustable gaps defined by the flexible bodies.

* * * * *